US006162813A

United States Patent [19]
Goulet et al.

[11] Patent Number: 6,162,813
[45] Date of Patent: Dec. 19, 2000

[54] ANTAGONISTS OF GONADOTROPIN RELEASING HORMONE

[75] Inventors: Mark Goulet; Robert J. Devita, both of Westfield; Matthew J. Wyvratt, Jr., Mountainside; Jonathan R. Young, Dayton, all of N.J.

[73] Assignee: Merck & Co., Inc., Rahway, N.J.

[21] Appl. No.: 09/180,656

[22] PCT Filed: May 16, 1997

[86] PCT No.: PCT/US97/08428

§ 371 Date: Nov. 12, 1998

§ 102(e) Date: Nov. 12, 1998

[87] PCT Pub. No.: WO97/44037

PCT Pub. Date: Nov. 27, 1997

Related U.S. Application Data

[60] Provisional application No. 60/017,152, May 20, 1996.

[30] Foreign Application Priority Data

Jun. 27, 1996 [GB] United Kingdom ................... 9613459

[51] Int. Cl.$^7$ ................... A61K 31/4704; C07D 215/20; C07D 215/22
[52] U.S. Cl. .......................... 514/312; 546/155; 546/156; 546/157
[58] Field of Search ..................................... 546/157, 156, 546/155; 514/312

[56] References Cited

U.S. PATENT DOCUMENTS 4,284,768   8/1981   Santilli .

FOREIGN PATENT DOCUMENTS

| | | |
|---|---|---|
| 0 101 897 A1 | 3/1984 | European Pat. Off. . |
| 0 219 292 A2 | 4/1987 | European Pat. Off. . |
| 0 679 642 A1 | 11/1995 | European Pat. Off. . |
| 2 711 992 A1 | 5/1995 | France . |
| 6 2395561 A2 | 12/1988 | Japan . |
| WO 93/10783 | 6/1993 | WIPO . |
| WO 93/11115 | 6/1993 | WIPO . |
| WO 95/28405 | 10/1995 | WIPO . |
| WO 95/29900 | 11/1995 | WIPO . |
| WO 97/14682 | 4/1997 | WIPO . |

OTHER PUBLICATIONS

Tetrahedron Ltrs., vol. 31, No. 24, pp. 3485–3488 (1990), by Veronese, et al.
J. Med. Chem. vol. 32, pp. 2036–2038 (1989), by Clark, et al.
J. Heterocyclic Chem, vol. 26, pp. 281–284 (1989), by Yamaguchi, et al.
Monatshefte Fur Chemie, vol. 113, pp. 751–760 (1982), by Stadlbauer, et al.
Vestn. Slov. Kem. Drus., vol. 33, No. 3, pp. 271–281 (1986), by Stadlbauer, et al.
Annu. Rev. Med., vol. 45, pp. 391–405 (1994), by Conn, et al.
Drugs of the Future, vol. 13, No. 8, pp. 761–787, by A. Dutta.
Current Opinion in Obstet. & Gyno., vol. 6, pp. 262–268 (1994), by R. Loy.
TEM, vol. 3, No. 1, pp. 30–34 (1992), by R. Barbieri.
Drugs, vol. 35, pp. 63–82, (1988), by Filicori, et al.
Human Reproduction, vol. 11, Suppl., pp. 89–101 (1996), by U. Cirkel.
Human Reproduction, vol. 11, Suppl., pp. 123–132 (1996), by G. Hodgen.

*Primary Examiner*—D. Margaret Seaman
*Attorney, Agent, or Firm*—Elliott Korsen; Mark R. Daniel

[57] ABSTRACT

There are disclosed compounds of formula (I)

and pharmaceutically acceptable salts thereof which are useful as antagonists of GnRH and as such may be useful for the treatment of a variety of sex-hormone related conditions in both men and women.

19 Claims, No Drawings

ANTAGONISTS OF GONADOTROPIN RELEASING HORMONE

This application is a 371 of PCT/US97/08428, May 16, 1997, and claims domestic priority to Provisional Application 60/017,152, filed May 20, 1996.

BACKGROUND OF THE INVENTION

The gonadotropin-releasing ho e (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females. GnRH agonists and antagonists have proven effective in the treatment of certain conditions which require inhibition of LH/FSH release. In particular, GnRH-based therapies have proven effective in the treatment of endometriosis, uterine fibroids, polycystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus. The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4,7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral administration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd.

Arylquinolone analogs have been described in the art and include those described in the following patents, patent applications and journal articles. JP-A-63-295561 discloses a class of 3-phenyl-2(1H)-quinolone derivatives, substituted at the 4-position by an unsubstituted straight or branched alkoxy group and at the 7-position by an unsubstituted straight or branched alkoxy group. These compounds are alleged to exhibit a strong inhibitory action on bone resorption and a stimulatory effect on ossification, and thus to be useful as therapeutic agents for the prevention and treatment of osteoporosis.

J. Heterocycl. Chem., 1989, 26, 281 discloses a range of 3-(2-methoxyphenyl)-2(1H)-quinolones possessing a halogen substituent in the 6- or 7-position and an optional carboxylic acid substituent at the 4-position. A family of 3-phenyl-2(1H)-quinolone derivatives, substituted at the 4-position by an amino or benzylamino group and at the 7-position by a methyl or methoxy group, is described in Monatsh. Chem., 1982, 113, 751 and Vestn. Slov. Kem. Drus., 1986, 33, 271.

WO 93/10783 and WO 93/11115 disclose a class of 2-(1H)-quinolone derivatives, substituted at the 3-position by an optionally substituted aryl substituent and are selective non-competitive antagonists of NMDA receptors and/or are antagonists of AMPA receptors, and are therefore of utility in the treatment of conditions, such as neurodegenerative disorders, convulsions or schizophrenia.

FR 2711992-Al discloses quinolone derivatives which are allegedly useful as antagonists of platelet activating factor.

SUMMARY OF THE INVENTION

The present invention relates to compounds which are non-peptide antagonists of GnRH which can be used to treat a variety of sex-hormone related conditions in men and women, to methods for their preparation, and to methods and pharmaceutical compositions containing said compounds for use in mammals.

Because of their activity as antagonists of the hormone GnRH, the compounds of the present invention are useful to treat a variety of sex-hormone related conditions in both men and women. These conditions include endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertophy. They are also useful as an adjunct to treatment of growth hormone deficiency and short stature, and for the treatment of systemic lupus erythematosis. Further, the compounds of the invention may be useful in in vitro fertilization and as contraceptives. The compounds may also be useful in combination with androgens, estrogens, progesterones, antiestrogens and antiprogestogens for the treatment of endometriosis, fibroids and in contraception. They may also be useful in combination with testosterone or other androgens or antiprogestogens in men as a contraceptive. The compounds may also be used in combination with an angiotensin-converting enzyme inhibitor such as Enalapril or Captopril, an angiotensin II-receptor antagonist such as Losartan or a renin inhibitor for the treatment of uterine fibroids. Additionally, the compounds of the invention may also be used in combination with bisphosphonates (bisphosphonic acids) and other agents, for the treatment and the prevention of disturbances of calcium, phosphate and bone metabolism, in particular, for the prevention of bone loss during therapy with the GnRH antagonist, and in combination with estrogens, progesterones and/or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4,7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

DETAILED DESCRIPTION OF THE INVENTION

The present invention relates to compounds of the general formula

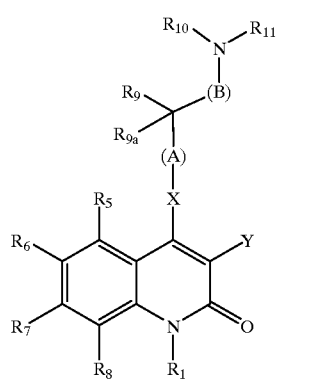

(I)

wherein:

A is a bond, $C_1$–$C_6$ alkyl, substituted $C_1$–$C_6$ alkyl, $C_2$–$C_6$ alkenyl, substituted $C_2$–$C_6$ alkenyl, $C_2$–$C_6$ alkynyl, substituted $C_2$–$C_6$ alkynyl, $C_1$–$C_6$ alkoxy, substituted $C_1$–$C_6$ alkoxy;

B is a bond, $C_1$–$C_6$ alkyl, substituted $C_1$–$C_6$ alkyl;

X is O, S, SO, $SO_2$, $NR_{12}$, $C(R_{13}R_{14})$, or can be absent;

Y is

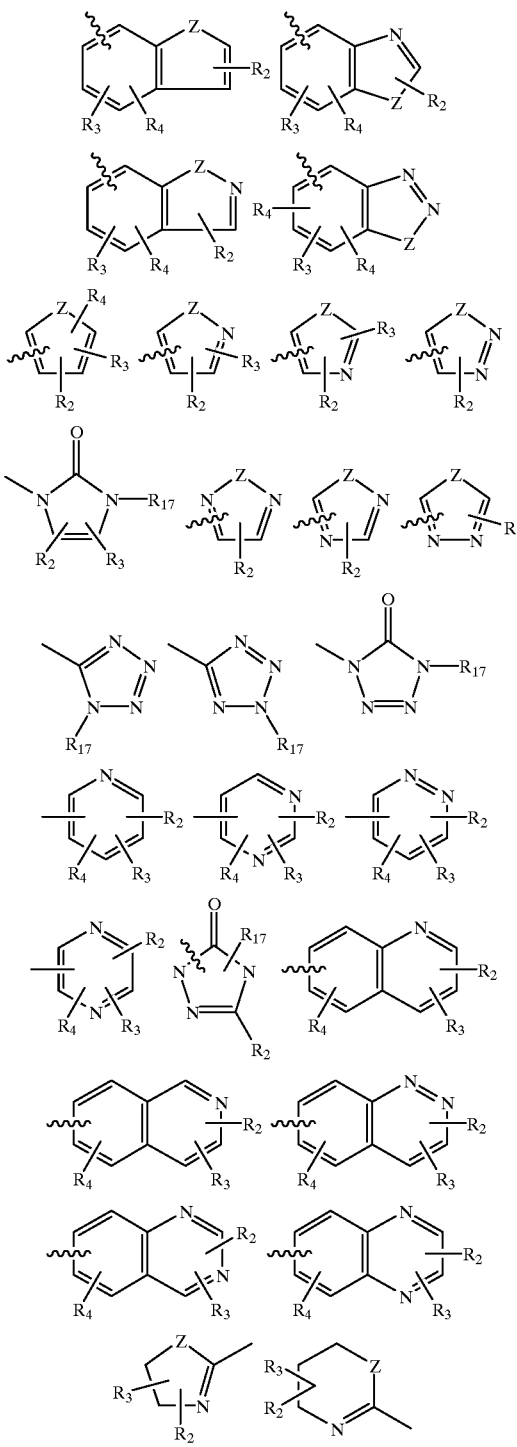

Z is O, S, or $NR_{12}$;

$R_1$ is H, $C_1$–$C_6$ alkyl, substituted $C_1$–$C_6$ alkyl, $C_3$–$C_6$ cycloalkyl, substituted $C_3$–$C_6$ cycloalkyl, aryl, substituted aryl, $C_1$–$C_6$ aralkyl, substituted $C_1$–$C_6$ aralkyl;

$R_2$, $R_3$ and $R_4$ are independently H, $C_1$–$C_6$ alkyl, substituted $C_1$–$C_6$ alkyl, $C_2$–$C_6$ alkenyl, substituted $C_2$–$C_6$ alkenyl, $C_2$–$C_6$ alkynyl, substituted $C_2$–$C_6$ alkynyl, CN, nitro, $C_1$–$C_3$ perfluoroalkyl, $C_1$–$C_3$ perfluoroalkoxy, aryl, substituted aryl, $C_1$–$C_6$ aralkyl, substituted $C_1$–$C_6$ aralkyl, $R_{15}O(CR_{13}R_{14})_p$—, $R_{16}C(O)O(CR_{13}R_{14})_p$—, $R_{15}OC(O)(CR_{13}R_{14})_p$—, —$(CR_{13}R_{14})_pS(O)_nR_{12}$, —$(CR_{13}R_{14})_pC(O)NR_{17}R_{18}$, —$(CR_{13}R_{14})_pNR_{17}C(O)R_{16}$, —$(CR_{13}R_{14})_pN(R_{17}R_{18})$ or halogen;

$R_5$, $R_6$, $R_7$ and $R_8$, independently are H, halogen, $C_1$–$C_6$ alkyl, substituted $C_1$–$C_6$ alkyl, $C_2$–$C_6$ alkenyl, substituted $C_2$–$C_6$ alkenyl, $C_2$–$C_6$ alkynyl, substituted $C_2$–$C_6$ alkynyl, aryl, substituted aryl, $C_1$–$C_6$ aralkyl, substituted $C_1$–$C_6$ aralkyl, $C_1$–$C_3$ perfluoroalkyl, $C_1$–$C_3$ perfluoroalkoxy, $R_{15}O(CR_{13}R_{14})_p$—, —$(CR_{13}R_{14})_pCN$, —$(CR_{13}R_{14})_pSO_nR_{12}$, —$(CR_{13}R_{14})_pSO_2N(R_{17}R_{18})$, —$(CR_{13}R_{14})_pN(R_{17}R_{18})$, —$(CR_{13}R_{14})_pN(R_{17})C(O)R_{16}$, —$(CR_{13}R_{14})_pN(R_{17})C(O)N(R_{17}R_{18})$, —$(CR_{13}R_{14})_pN(R_{17})SO_2N(R_{17}R_{18})$, —$(CR_{13}R_{14})_pN(R_{17})SO_2R_{12}$, —$(CR_{13}R_{14})_pC(O)OR_{15}$, —$(CR_{13}R_{14})_pOC(O)R_{16}$, —$(CR_{13}R_{14})_pC(O)N(R_{17}R_{18})$ —$(CR_{13}R_{14})_pOC(O)N(R_{17}R_{18})$, —$(CR_{13}R_{14})_pN(R_{17})C(O)OR_{15}$, or

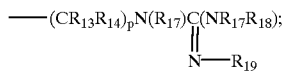

$R_9$ and $R_{9a}$ are independently H, $C_1$–$C_6$ alkyl, substituted $C_1$–$C_6$ alkyl, aryl, substituted aryl, $C_1$–$C_6$ aralkyl, substituted $C_1$–$C_6$ aralkyl; or $R_{10}$ is H, $C_1$–$C_6$ alkyl, substituted $C_1$–$C_6$ alkyl, aryl, substituted aryl, $C_1$–$C_6$ aralkyl, substituted $C_1$–$C_6$ aralkyl; or $R_{11}$ is H, $C_1$–$C_6$ alkyl, substituted $C_1$–$C_6$ alkyl, —$(CR_{13}R_{14})_pC(O)OR_{15}$; or $R_9$ and $R_{9a}$ can be taken together to form a carbocyclic ring, saturated or unsaturated, of 3–7 variously substituted carbon atoms, or;

$R_9$ and $R_{10}$ can be taken together to form a heterocyclic ring, saturated or unsaturated, of 4–7 atoms containing 1–3 heteroatoms selected from O, N, and S, or;

($R_9$ and $R_{10}$) and ($R_{9a}$ and $R_{11}$) can be taken together to form a heterobicyclic ring, with each ring being independently saturated or unsaturated, of 4–7 atoms containing 1–3 heteroatoms selected from O, N, and S;

$R_{12}$ is H, $C_1$–$C_6$ alkyl, substituted $C_1$–$C_6$ alkyl, aryl, substituted aryl, $C_1$–$C_6$ aralkyl, substituted $C_1$–$C_6$ aralkyl;

$R_{13}$ and $R_{14}$ are independently H, $C_1$–$C_6$ alkyl, substituted $C_1$–$C_6$ alkyl, aryl, substituted aryl, $C_1$–$C_6$ aralkyl, substituted $C_1$–$C_6$ aralkyl;

$R_{15}$ is H, $C_1$–$C_6$ alkyl, substituted $C_1$–$C_6$ alkyl, aryl, substituted aryl, $C_1$–$C_6$ aralkyl, substituted $C_1$–$C_6$ aralkyl;

$R_{16}$ is H, $C_1$–$C_6$ alkyl, substituted $C_1$–$C_6$ alkyl, aryl, substituted aryl, $C_1$–$C_6$ aralkyl, substituted $C_1$–$C_6$ aralkyl;

$R_{17}$ and $R_{18}$ are independently H, $C_1$–$C_6$ alkyl, substituted $C_1$–$C_6$ alkyl, $C_3$–$C_6$ cycloalkyl, substituted $C_3$–$C_6$ cycloalkyl, aryl, substituted aryl, $C_1$–$C_6$ aralkyl, substituted $C_1$–$C_6$ aralkyl, or taken together form a carbocyclic ring(s) of 4–7 carbon atoms each;

$R_{19}$ is H, $C_1$–$C_6$ alkyl, substituted $C_1$–$C_6$ alkyl or —CN;

n is 0, 1, or 2;

p is 0, 1, 2, 3 or 4 the alkyl, cycloalkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, C(O)OR$_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

Unless otherwise stated or indicated, the following definitions shall apply throughout the specification and claims.

When any variable (e.g., aryl, heterocycle, $R_1$, etc.) occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, etc.

The term "aryl" includes phenyl and naphthyl. Preferably, aryl is phenyl.

The term "halogen" or "halo" is intended to include fluorine, chlorine, bromine and iodine.

The term "heterocycle" or "heterocyclic ring" is defined by all non-aromatic, heterocyclic rings of 3–7 atoms containing 1–3 heteroatoms selected from N, O, and S, such as oxirane, oxetane, tetrahydrofuran, tetrahydropyran, pyrrolidine, piperidine, tetrahydropyridine, tetrahydropyrimidine, tetrahydrothiophene, tetrahydrothiopyran, morpholine, hydantoin, valerolactam, pyrrolidinone, and the like.

The term "heteroaryl" is intended to include the compounds shown below:

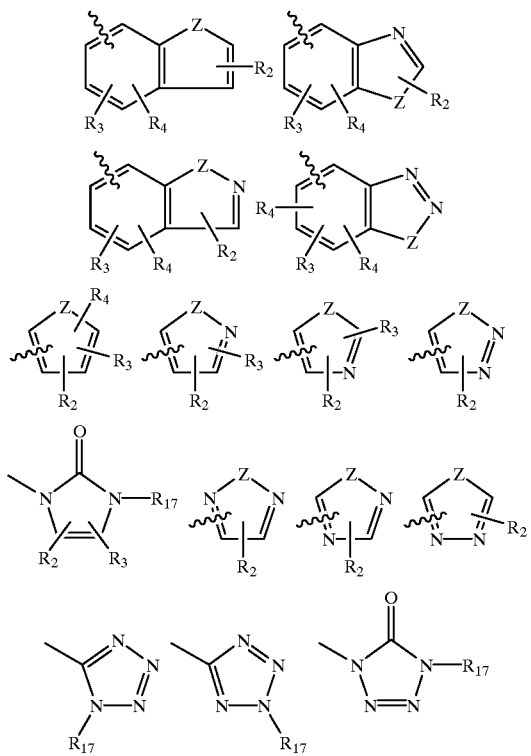

where Z is: O, S, or $NR_{12}$.

In addition, it is well known to those skilled in the art that many of the foregoing heterocyclic groups can exist in more than one taotomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, omithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

As used herein, the term "composition" is intended to encompass a product comprising the specified ingredients in the specified amounts, as well as any product which results, directly or indirectly, from combination of the specified ingredients in the specified amounts.

The compounds of the invention are prepared by the following reaction schemes. All substituents are as defined above unless indicated otherwise.

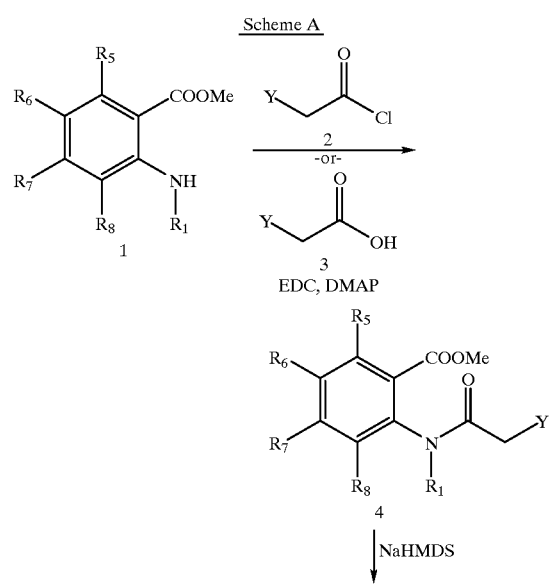

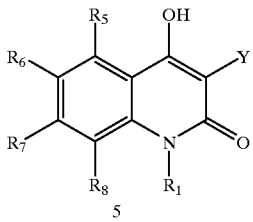

Reaction Scheme A

As shown in reaction Scheme A, treatment of amino ester (1) with a heteroaryl acetyl chloride (2) in an inert organic solvent such as dichloroethane, chloroform, methylene chloride or the like at a temperature of 25–80° C. for a period of 30 minutes to 4 hours gives the corresponding amide (4). Alternatively, treatment of amine (1) and a heteroarylacetic acid (3) with the coupling reagent 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, NN-dimethylformamide, or mixtures thereof at or near room temperature for a period of 3–24 hours to provides the corresponding amide derivative (4). Cyclization of amide (4) is effected by treatment with a strong base such as sodium bis(trimethylsilyl)amide, lithium bis(trimethylsilyl)amide or the like in an inert organic solvent such as tetrahydrofuran at a temperature of −20°–25° C. for a period of 2–4 hours to give quinolone (5).

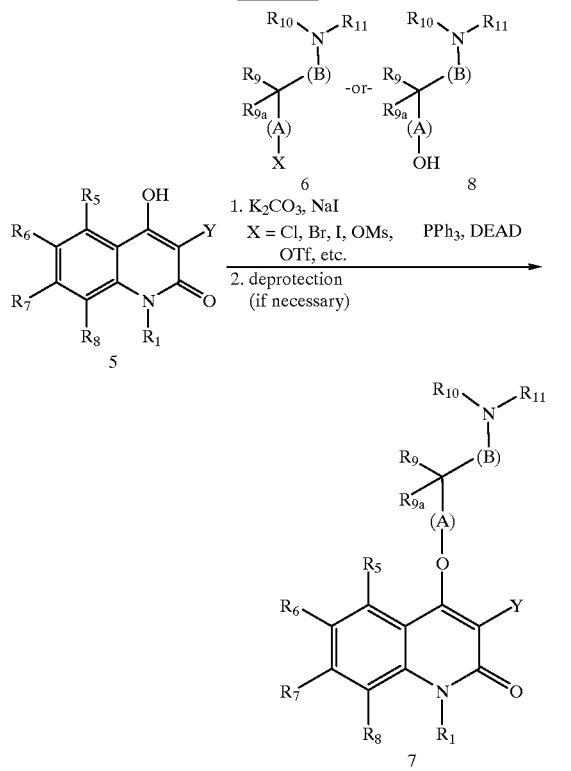

Reaction Scheme B

As shown in reaction Scheme B, treatment of the 4-hydroxyquinolone (5) with an alkylamine containing a halogen or sulfonate leaving group (6) and a suitable base such as potassium carbonate, sodium carbonate, sodium bicarbonate, DBU or the like along with the catalyst sodium iodide in an inert organic solvent such as N,N-dimethylformamide, tetrahydrofuran, acetonitrile or the like at or around 80° C. for a period of 4–24 hours provides the ether derivative (7). As an alternative, a suitably protected amino alcohol (8) may be coupled to (5) by treatment under Mitsunobu reaction conditions with triphenylphosphine and an activating agent such as diethyl azodicarboxylate, diisopropyl azodicarboxylate or the like in an inert solvent such as tetrahydrofuran, toluene, chlorobenzene or the like at ambient temperature for a period of 4–64 hours to give (7). After coupling, the amino group can be deprotected by any method suitable to the protecting group used and compatible with the functionality present in (7). For example, a t-butyl carbamate group can be removed by treatment with a protic acid such as trifluoroacetic acid, with or without added anisole, in an inert organic solvent such as methylene chloride at ambient temperature for a period of 30 minutes to 4 hours to provide the corresponding amine.

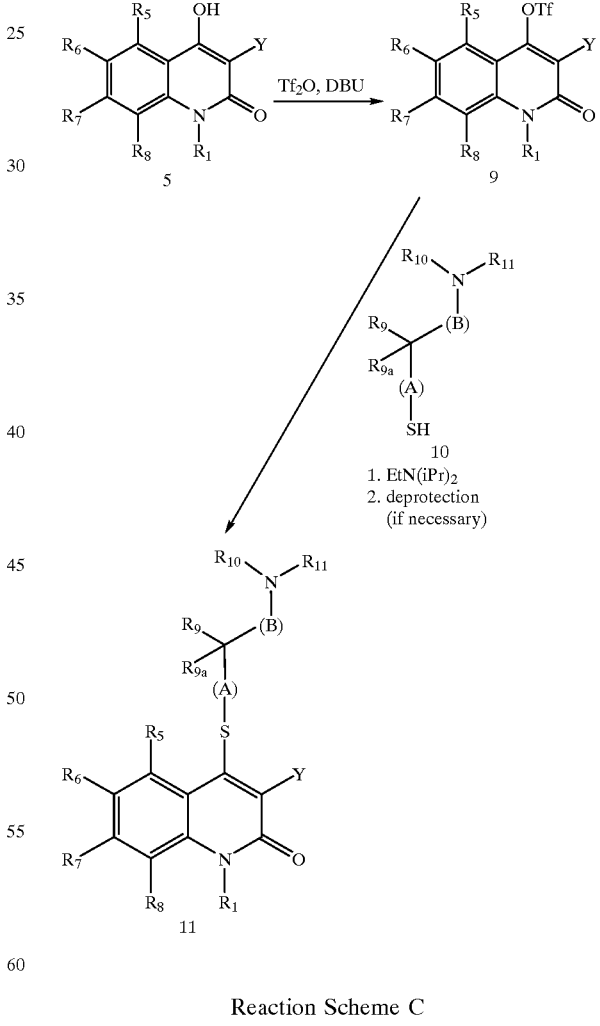

Reaction Scheme C

As shown in reaction Scheme C, the 4-hydroxyquinolone structure (5) may be modified by conversion to a sulfonate leaving group such as the trifluoromethanesulfonate (9) upon treatment with trifluoromethane-sulfonic anhydride in an inert organic solvent such as methylene chloride and an amine base such as diazabicycloundecene, 2,6-lutidine, pyridine or the like at or below room temperature for a period of 30 minutes to 2 hours. Reaction of (9) with an appropriate thiol (10) and an amine base such as diisopropylethylamine, triethylamine or the like in an inert organic solvent such as NN-dimethylformamide at or below room temperature for a period of 4–24 hours gives the thioether analog (11).

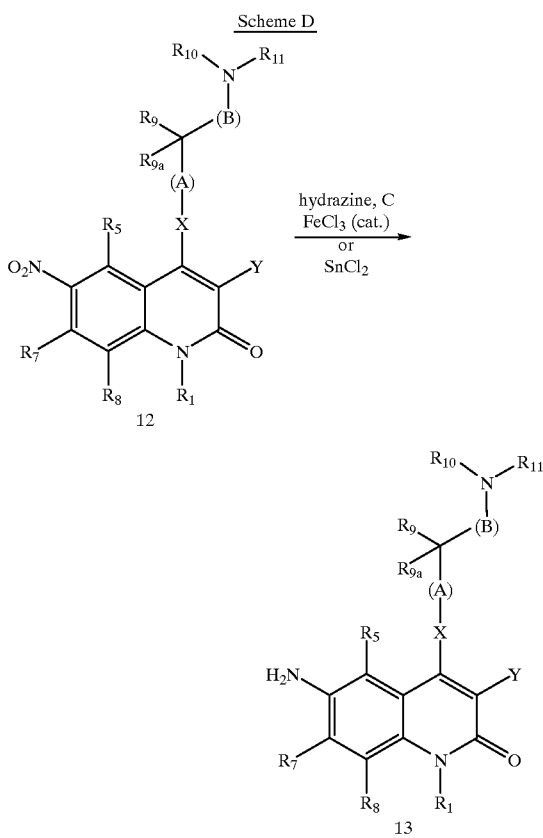

Reaction Scheme D

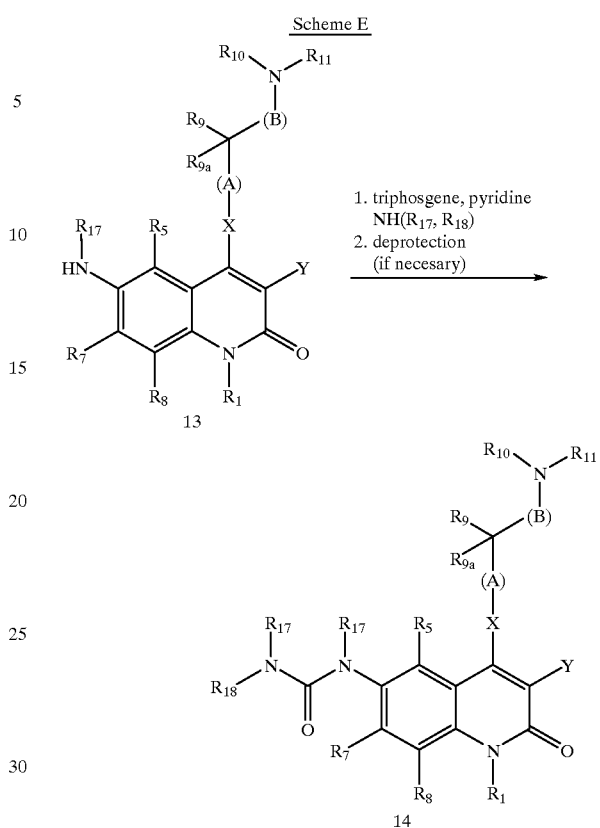

Reaction Scheme E

As shown in reaction Scheme E, amines such as (13) can be converted to the corresponding urea derivatives (14) by treatment with an appropriate acylating agent such as phosgene, triphosgene, carbonyldiimidazole or the like, with or without an amine base such as pyridine in an inert organic solvent such as methylene chloride, chloroform, dichloroethane or the like together with the desired primary or secondary amine at 0°–25° C. for a period of 1–48 hours.

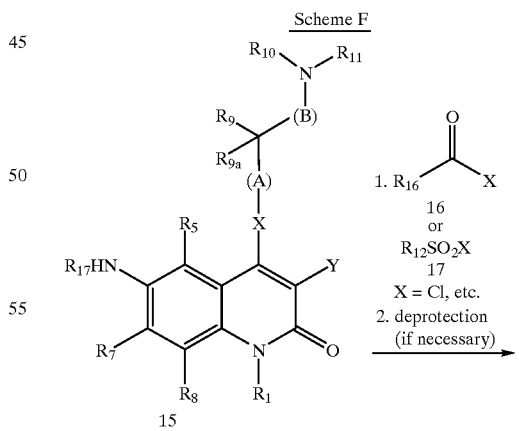

Reaction Scheme D

As shown in reaction Scheme D, nitro groups appended to these structures, such as in (12), can be reduced to the corresponding amines (13) by treatment with hydrazine and a reduction catalyst such as iron (III) chloride and carbon in an inert organic solvent such as methanol, ethanol or the like at a temperature of 65°–100° C. for a period of 5–20 hours. Alternatively, treatment of (12) with tin(II)chloride dihydrate in a polar solvent such as ethanol or methanol at a temperature of 70°–80° C. for a period of 30 minutes to 4 hours gives the reduced, amino derivative (13).

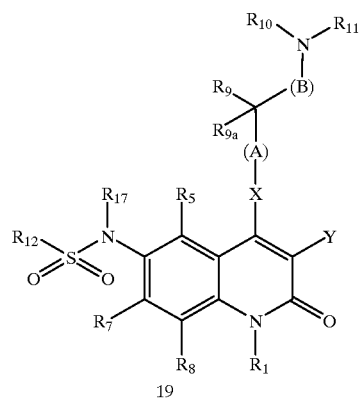

19

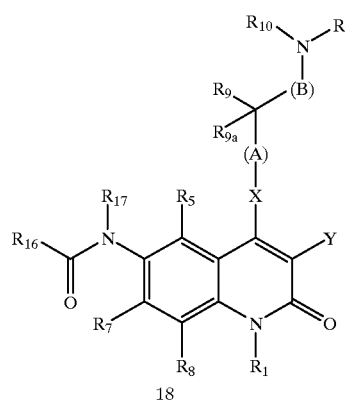

18

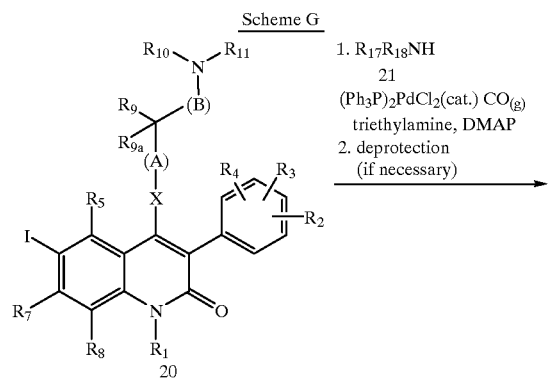

Scheme G

1. $R_{17}R_{18}NH$
   21
   $(Ph_3P)_2PdCl_2$(cat.) $CO_{(g)}$
   triethylamine, DMAP
2. deprotection
   (if necessary) →

20

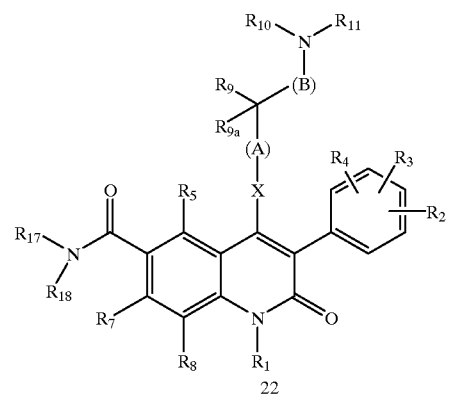

22

Reaction Scheme F

As shown in reaction Scheme F, amines such as (15) can be converted to the corresponding amide (18) or sulfonamide derivatives (19) by treatment with an appropriate acylating agent such as an acetyl chloride, acid anhydride, sulfonylchloride, sulfonic anhydride or the like, with or without an amine base such as pyridine, in an inert organic solvent such as methylene chloride, chloroform, dichloroethane, benzene, toluene, chlorobenzene or the like at 0°–100° C. for a period of 1–10 hours.

Reaction Scheme G

As shown in Scheme G, iodides such as (20) can be converted to the corresponding amide (22) by treatment with an appropriate amine (21) and a palladium catalyst such as dichlorobis(triphenylphosphine)palladium(II) in the presence of an amine base such as triethylamine in an inert organic solvent such as N,N-dimethylformamide, or the like, under an atmosphere of carbon monoxide at 90° C. for a period of 5–25 hours.

Scheme H

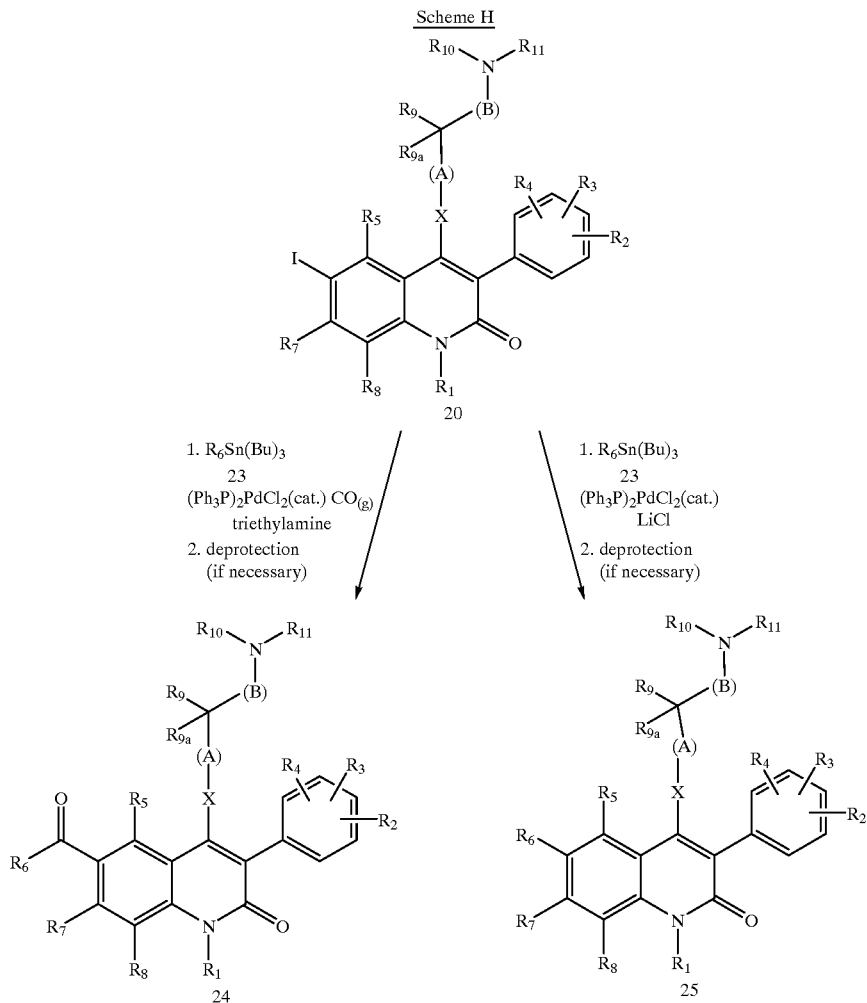

Reaction Scheme H

As shown in Reaction Scheme H, iodide (20) can be coupled with alkyl-, vinyl-, aryl- and heteroaryl-stannanes (23) using an appropriate palladium catalyst such as dichlorobis(triphenylphosphine) palladium(II) in an inert organic solvent such as N,N-dimethyl formamide, toluene, or the like, at a temperature of 80–110° C. with or without the presence of carbon monoxide to provide ketones (24) and carbon-linked derivatives (25), respectively.

Scheme I

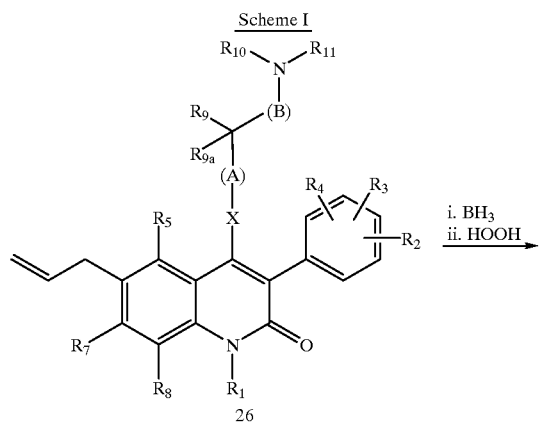

Reaction Scheme I

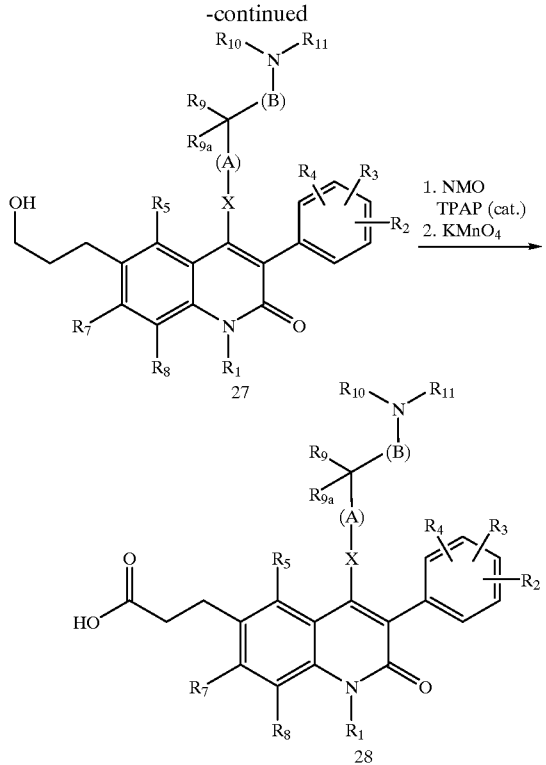

As shown in Scheme I, the allyl derivative (26) can be converted to primary alcohol (27) by treatment with borane or a suitable alkylborane reagent in an inert solvent such as tetrahydrofuran followed by exposure to a mild oxidant such as hydrogen peroxide. Alcohols such as (27) can be further oxidized by treatment with tetrapropylammonium perruthenate(VII) and 4-methylmorpholine-N-oxide or similarly mild oxidants in an organic solvent such as methylene chloride at room temperature for a period of 1 to 5 hours to give the corresponding aldehyde. Further oxidation to the carboxylic acid can be conducted with a strong oxidant such as potassium permanganate to give acids such as (28).

Scheme J

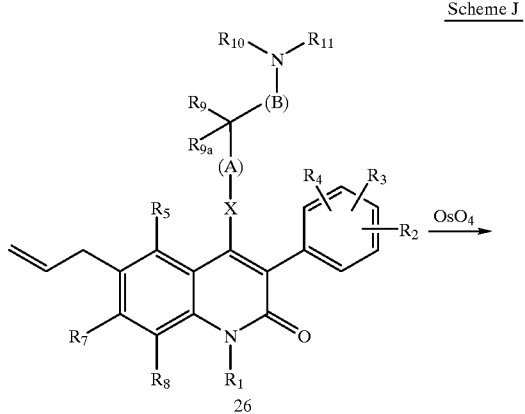

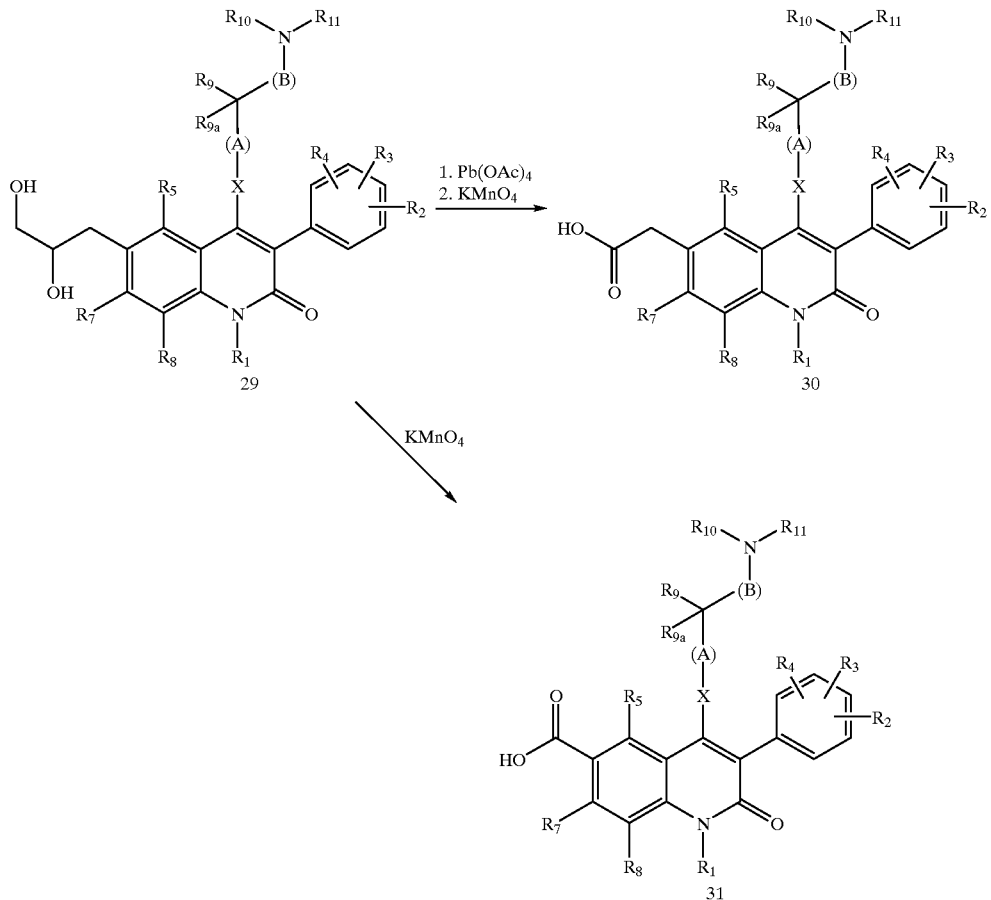

Reaction Scheme J

As shown in Scheme J, the allyl derivative (26) can be converted to the diol (29) by treatment with osmium tetraoxide with or without a co-oxidant such as 4-methylmorpholine-N-oxide in an inert solvent such as tetrahydrofuran, tert-butanol, water or mixtures thereof at room temperature for a period of 15 minutes to 5 hours. Diols such as (29) can be further oxidized by treatment with lead (IV) acetate in an inert solvent such as methanol pyridine or mixtures thereof at room temperature for a period of 10 minutes to 2 hours to give the corresponding aldehyde derivative. Further oxidation to the carboxylic acid can be conducted with a strong oxidant such as potassium permanganate to give acids such as (30).

Alternatively, treatment of diol (29) with a strong oxidant such as potassium permanganate, ruthenium tetraoxide or the like can give the benzoic acid product (31) directly.

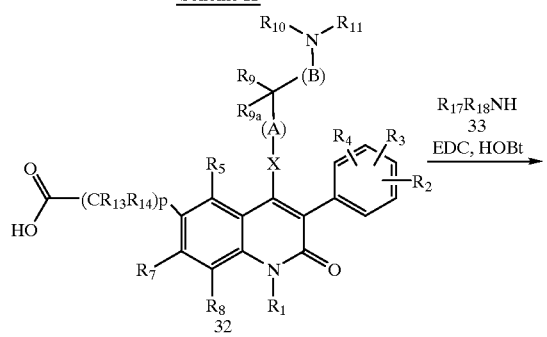

Scheme K

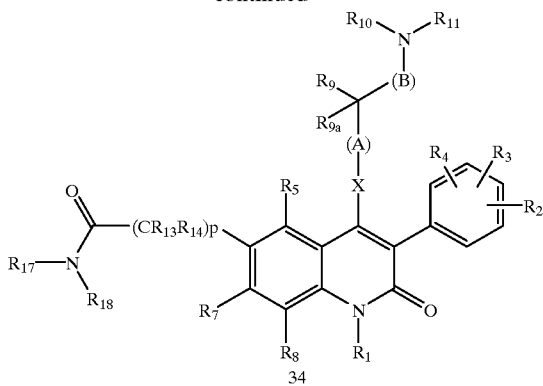

Reaction Scheme K

As shown in Scheme K, treatment of carboxylic acid (32) and an appropriate amine such as (33) with the coupling reagent 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours provides the corresponding amide derivative (34).

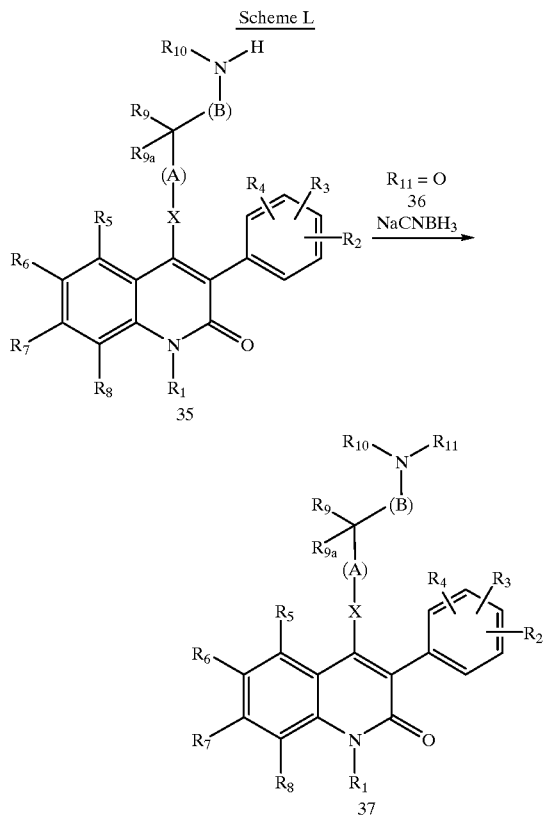

Reaction Scheme L

As shown in Scheme L, amines such as (35) can undergo reductive amination with carbonyl-containing compounds like (36) by treating the pair with a dessicant such as molecular seives or magnesium sulfate and an acid catalyst such as acetic acid in an inert organic solvent such as methanol, chloroform or the like followed by a reducing agent such as sodium cyanoborohydride, sodium borohydride, or hydrogen and an appropriate metal catalyst to give derivative (37).

The compounds of the present invention are useful in the treatment of various sex-hormone related conditions in men and women. This utility is manifested in their ability to act as antagonists of the neuropeptide hormone GnRH as demonstrated by activity in the following in vitro assays.

Human GnRH Receptor Binding Assay

Crude membranes prepared from CHO cells expressing human GnRH receptors were the sources for GnRH receptor. [$^{125}$I]Buserelin (a peptidyl GnRH analog) was used as the radiolabelled ligand. The binding activity was determined as an $IC_{50}$ which is the antagonist concentration required to inhibit the specific binding of [$^{125}$I]buserelin to GnRH receptors by 50%.

Rat Pituitary GnRH Receptor Binding Assay:

Crude plasma membranes prepared from rat pituitary tissues were incubated in a Tris.HCl buffer (50 mM, pH 7.5) containing bovine serum albumin (0.1%), [I-125]D-t-Bu-Ser6-Pro9-ethyl amide-GnRH, and the desired concentration of a test compound. The assay mixtures were incubated at 4° C. for 90–120 minutes followed by rapid filtration and repeated washings through a glass fiber filter. The radioactivity of membrane bound radioligands was determined in a gamma-counter. From this data, the $IC_{50}$ of the radioligand binding to GnRH receptors in the presence of test compound was estimated.

Inhibition of LH Release Assay:

Active compounds from the GnRH receptor binding assay were further evaluated with an in vitro LH release assay to confirm their antagonist activity (blocking GnRH-induced LH release).

1. Sample Preparation

The compounds to be assayed were dissolved and diluted in DMSO. The final concentration of DMSO in the incubation medium was 0.5%.

2. Assay

The Wistar male rats (150–200 grams) were obtained from Charles River Laboratories (Wilmington, Mass.). Rats were maintained at a constant temperature (25° C.) on a 12-hr light, 12-hr dark cycle. Rat chow and water were available ad libitum. The animals were sacrificed by decapitation and pituitary glands were aseptically removed and placed in Hank's Balanced Salt Solution (HBSS) in a 50-mL polypropylene centrifuge tube. The collection tube was centrifuged for 5 min at 250×g, and HBSS was removed by aspiration. Pituitary glands were transferred to a disposable petri plate and minced with a scalpel. The minced tissue was then transferred to a 50-mL disposable centrifuge tube by suspending the tissue fragments in three successive 10-mL aliquots of HBSS containing 0.2% collagenase and 0.2% hyaluronidase. The cell dispersion was carried out in a water bath at 37° C. with gentle stirring for 30 min. At the end of the incubation, the cells were aspirated 20 to 30 times with a pipet and the undigested pituitary fragments were allowed to settle for 3 to 5 min. The suspended cells were removed by aspiration, and then subjected to a 1200×g centrifugation for 5 min. The cells were then resuspended in Culture medium. The undigested pituitary fragments were treated with 30 mL aliquots of the digestion enzymes as above for a total of 3 digestions with the collagenase/hyaluronidase mixture. The resulting cell suspensions were pooled, counted and diluted to a concentration of 3×10⁵ cells/ml, and 1.0 ml of this suspension was placed in each well of a 24-well tray (Costar, Cambridge, Mass.). Cells were maintained in a humidified 5% $CO_2$—95% air atmosphere at 37° C. for 3 to 4 days. The culture medium consisted of DMEM containing 0.37% $NaHCO_3$, 10% horse serum, 2.5% fetal bovine serum, 1% non-essential amino acids, 1% glutamine, and 0.1% gentamycin. On the day of an experiment, cells were washed three times 1 ½ hrs prior to and two more times immediately before the start of the experiment with DMEM containing 0.37% $NaHCO_3$, 10% horse serum, 2.5% fetal bovine serum, 1% non-essential amino acids(100×), 1% glutamine(100×), 1% Penicillin/Streptomycin(10,000 Units of Penicillin and 10,000 micrograms of Streptomycin per ml), and 25 mM HEPES, pH 7.4. LH release was initiated by adding 1 ml of fresh medium containing test compounds in the presence of 2 nM GnRH to each well in duplicate. Incubation was carried out at 37° C. for 3 hr. After incubation, medium was removed and centrifuged at 2,000×g for 15 min to remove any cellular material. The supernatant fluid was removed and assayed for LH content with a double antibody RIA procedure using materials obtained from Dr. A. F. Parlow (Harbor-UCLA Medical Center, Torrance, Calif.).

The compounds of formula I are useful in a number of areas affected by GnRH. They may be useful in sex-hormone related conditions, sex-hormone dependent cancers, benign prostatic hypertrophy or myoma of the uterus. Sex-hormone dependent cancers which may benefit from the administration of the compounds of this invention include prostatic cancer, uterine cancer, breast cancer and pituitary gonadotrophe adenomas. Other sex-hormone dependent conditions which may benefit from the administration of the compounds of this invention include endometriosis, polycystic ovarian disease, uterine fibroids and precocious puberty. The compounds may also be used in combination with an angiotensin-converting enzyme inhibitor such as Enalapril or Captopril, an angiotensin II-receptor antagonist such as Losartan or a renin inhibitor for the treatment of uterine fibroids.

The compounds of the invention may also be useful for controlling pregnancy, as a contraceptive in both men and women, for in vitro fertilization, in the treatment of premenstrual syndrome, in the treatment of lupus erythematosis, in the treatment of hirsutism, in the treatment of irritable bowel syndrome and for the treatment of sleep disorders such as sleep apnea.

A further use of the compounds of this invention is as an adjunct to growth hormone therapy in growth hormone deficient children. The compounds may be administered with growth hormone or a compound which increases the endogenous production or release of growth hormone. Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89/07110, and PCT Patent Pub. No. WO 89/07111) and GHRP-2 (described in PCT Patent Pub. No. WO 93/04081), as well as hexarelin (*J. Endocrinol Invest.*, 15(Suppl 4), 45 (1992)). Other compounds which stimulate the release of endogenous growth hormone are disclosed, for example, in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; *Science*, 260, 1640–1643 (Jun. 11, 1993); *Ann. Rep. Med. Chem.*, 28, 177–186 (1993); *Bioorg. Med. Chem. Ltrs.*, 4(22), 2709–2714 (1994); and *Proc. Natl. Acad. Sci. USA* 92, 7001–7005 (July 1995).

Representative preferred growth hormone secretagoues employed in the present combination include the following:
1) N-[1(R)-[(1,2-Dihydro-1-methanesulfonylspiro[3H-indole-3,4'-piperidin]-1'-yl)carbonyl]-2-(1H-indol-3-yl)ethyl]-2-amino-2-methylpropanamide;
2) N-[1(R)-[(1,2-Dihydro-1-methanecarbonylspiro[3H-indole-3,4'-piperidin]-1'-yl)carbonyl]-2-(1H-indol-3-yl)ethyl]-2-amino-2-methylpropanamide;
3) N-[(R)-[(1,2-Dihydro-1-benzenesulfonylspiro[3H-indole-3,4'-piperidin]-1'-yl)carbonyl]-2-(1H-indol-3-yl)ethyl]-2-amino-2-methylpropanamide;
4) N-[1(R)-[(3,4-Dihydro-spiro[2H-1-benzopyran-2,4'-piperidin]-1'-yl) carbonyl]-2-(1H-indol-3-yl)ethyl]-2-amino-2-methylpropanamide;
5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methylpropanamide;
6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;
7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate;
8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;
9) N-[1(R)-[(1,2-Dihydro-1-methanesulfonyl-5-fluorospiro[3H-indole-3,4'-piperidin]-1'-yl)carbonyl]-2-(phenylmethyloxy)ethyl]-2-amino-2-methylpropanamide;
10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;
11) N-[1(R)-[(1,2-Dihydro-1-methanesulfonylspiro[3H-indole-3,4'-piperidin]-1'-yl)carbonyl]-3-phenylpropyl]-2-amino-2-methylpropanamide;
12) N-[1(R)-[(1,2-Dihydro-1-methanesulfonylspiro[3H-indole-3,4'-piperidin]-1'-yl)carbonyl]-3-cyclohexylpropyl]-2-amino-2-methylpropanamide;
13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;
14) N-[1(R)-[(1,2-Dihydro-1-methanesulfonylspiro[3H-indole-3,4-piperidin]-1'-yl)carbonyl]-2-(5-fluoro-1H-indol-3-yl)ethyl]-2-amino-2-methylpropanamide;
15) N-[1(R)-[(1,2-Dihydro-1-methanesulfonyl-5-fluorospiro[3H-indole-3,4'-piperidin]-1'-yl)carbonyl]-2-

(5-fluoro-1H-indol-3-yl)ethyl]-2-amino-2-methylpropanamide;

16) N-[1(R)-[(1,2-Dihydro-1-(2-ethoxycarbonyl)methylsulfonylspiro-[3H-indole-3,4'-piperidin]-1'-yl)carbonyl]-2-(1H-indol-3-yl)ethyl]-2-amino-2-methylpropanamide;

17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Bisphosphonates (bisphosphonic acids) are known to inhibit bone resorption and are useful for the treatment of bone lithiasis as disclosed in U.S. Pat. No. 4,621,077 to Rosini, et al.

The literature discloses a variety of bisphosphonic acids which are useful in the treatment and prevention of diseases involving bone resorption. Representative examples may be found in the following: U.S. Pat. No. 3,251,907; U.S. Pat. No. 3,422,137; U.S. Pat. No. 3,584,125; U.S. Pat. No. 3,940,436; U.S. Pat. No. 3,944,599; U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,578,376; U.S. Pat. No. 4,621,077; U.S. Pat. No. 4,624,947; U.S. Pat. No. 4,746,654; U.S. Pat. No. 4,761,406; U.S. Pat. No. 4,922,007; U.S. Pat. No. 4,942,157; U.S. Pat. No. 5,227,506; U.S. Pat. No. 5,270,365; EPO Patent Pub. No. 0,252,504; and J. Org. Chem., 36, 3843 (1971).

The preparation of bisphosphonic acids and halo-bisphosphonic acids is well known in the art. Representative examples may be found in the above mentioned references which disclose the compounds as being useful for the treatment of disturbances of calcium or phosphate metabolism, in particular, as inhibitors of bone resorption.

Preferred bisphosphonates are selected from the group of the following compounds: alendronic acid, etidrononic acid, clodronic acid, pamidronic acid, tiludronic acid, risedronic acid, 6-amino-1-hydroxy-hexylidene-bisphosphonic acid, and 1-hydroxy-3(methylpentylamino)-propylidene-bisphosphonic acid; or any pharmaceutically acceptable salt thereof. A particularly preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSAMAX®.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4,7β-dimethyl-16β-(4-chlorophenoxy)-5β-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 10 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples illustrate the preparation of some of the compounds of the invention and are not to be construed as limiting the invention disclosed herein.

EXAMPLE 1

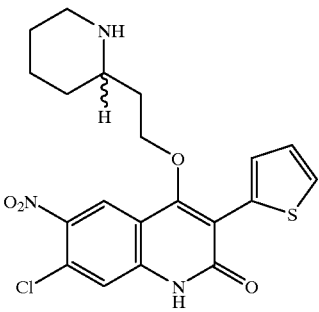

7-chloro-6-nitro-4-(2-piperidin-2-yl-ethoxy)-3-thiophen-2-1-1H-quinolin-2-one

Step 1A 4-chloro-5-nitro-2-(2-thiophen-2-yl-acetylamino)-benzoic acid methyl ester To a suspension of 2-amino-4-chloro-5-nitrobenzoic acid methyl ester (221 mg in 2.5 mL of dry 1,2-dichloroethane) was added a solution of thiophen-2-yl-acetyl chloride (169 mg in 3.0 mL dry 1,2-dichloroethane) and the mixture heated at reflux on an oil bath. After 18 hours, the reaction was cooled and the solvent removed in vacuo. Recrystallization of the crude product from methanol gave the title compound (230 mg).

Step 1B 7-chloro-4-hydroxy-6-nitro-3-thiophen-2-yl-1H-quinolin-2-one

To a solution of 4-chloro-5-nitro-2-(2-thiophen-2-yl-acetylamino)-benzoic acid methyl ester (130 mg in 4.0 mL dry tetrahydrofuran) at 0° C. was added dropwise a solution of sodium bis(trimethylsilyl)amide (0.92 mL of a 1.0M solution in tetrahydrofuran) and the mixture warmed to room temperature. After 3 hours, the reaction was quenched by the addition of 6N hydrochloric acid. The slurry was stirred for 10 minutes then filtered and washed with ice cold acetonitrile. The residue was dried in vacuo to give the title compound (79 mg).

Step 1C 2-[2-(7-chloro-6-nitro-2-oxo-3-thiophen-2-yl-1,2-dihydro-quinolin-4-yloxy)-ethyl]-piperidine-1-carboxylic acid tert-butyl ester To a solution of 7-chloro-4-hydroxy-6-nitro-3-thiophen-2-yl-1H-quinolin-2-one (50 mg in 2.5 mL of tetrahydrofuran) at 0° C. was added 44 mg of 2-(2-hydroxyethyl)-piperidine-1-carboxylic acid tert-butyl ester and 63 mg of triphenylphosphine followed by 0.04 mL of diethyl azodicarboxylate and the mixture warmed to room temperature. After 24 hours, the solvents were removed in vacuo and the residue purified by flash chromatography on silica gel (hexane:ethyl acetate, 90:10; then 80:20; then 60:40) to give the title compound (44 mg).

Step 1D 7-chloro-6-nitro-4-(2-piperidin-2-yl-ethoxy)-3-thiophen-2-yl-1H-quinolin-2-one To a solution of 2-[2-(7-chloro-6-nitro-2-oxo-3-thiophen-2-yl-1,2-dihydro-quinolin-4-yloxy)-ethyl]-piperidine-1-carboxylic acid tert-butyl ester (45 mg in 2.0 mL methylene chloride) was added 2 drops of anisole followed by 1.0 mL of trifluoroacetic acid and the mixture stirred at room temperature. After 45 minutes the solvents were removed in vacuo and the resulting residue purified by flash chromatography on silica gel (methylene chloride:methanol, 95:5) to give the title compound (25 mg).

PREPARATION OF SYNTHETIC INTERMEDIATES 2-amino-4-chloro-5-nitrobenzoic acid methyl ester Step A: 2-acetylamino-4-chloro-5-nitrobenzoic acid methyl ester To a solution of 3 mL conc. sulfuric acid and 0.40 mL of 90% nitric acid at 0° C. was added 2-acetylamino-4-chlorobenzoic acid methyl ester (1.5 g) in three portions over a period of 20 minutes. This was stirred at 0° C. for 30 minutes then allowed to warm to room temperature for an additional 1 hour. At this time the reaction was poured into 50 mL of an ice/water mixture and extracted with ethyl acetate (3×50 mL). The combined organics were washed sequentially with water (2×50 mL), 10% sodium bicarbonate (2×50 mL) and brine (50 mL) then dried over magnesium sulfate and concentrated in vacuo. Recrystallization of the crude product from methanol gave the title compound (1.02 g).

Step B: 2-amino-4-chloro-5-nitrobenzoic acid methyl ester

To a solution of 2-acetylamino-4-chloro-5-nitrobenzoic acid methyl ester (1.02 g in 15 mL methanol) was added 1 mL of conc. sulfuric acid and the mixture heated to reflux on an oil bath. After 1 hour, the mixture was concentrated in vacuo and the resulting solid dissolved in 200 mL ethyl acetate. This was then washed with 10% sodium bicarbonate (2×100 mL) and brine (100 mL) and the organics dried over magnesium sulfate. The concentrate was recrystallized from methanol to give the title compound (0.82 g).

2-(2-hydroxyethyl)-piperidine-1-carboxylic acid tert-butyl ester

Step AA: 2-(diazoacetyl)piperidine-1-carboxylic acid tert-butyl ester

To a solution of piperidine-1,2-dicarboxylic acid 1-tert-butyl ester (3.0 g in a mixture of 26 mL dry tetrahydrofuran and 26 mL dry diethyl ether) at −10° C. was added 1.91 mL of triethylamine followed by the dropwise addition of 1.78 mL isobutyl chloroformate. The reaction was stirred at −10° C. for 30 minutes then warmed to 0° C. Over the next hour, 26 mL of a solution of diazomethane in diethyl ether was added (prepared from: 8.0 g Diazald® in 70 mL diethyl ether; 4 g potassium hydroxide; 20 mL 2-(2-ethoxyethoxy) ethanol; 6 mL water and 12 mL diethyl ether using a mini Diazald Kit) and the mixture allowed to stir at room temperature for an additional 2 hours. At this time the reaction was quenched by the addition of 3 mL acetic acid at 0° C. This was then diluted with 100 mL water and 100 mL diethyl ether, the layers separated and the aqueous portion extracted with (2×75 mL) diethyl ether. The combined organics were washed with water (75 mL), saturated sodium bicarbonate (2×75 mL) and brine (75 mL) then dried over magnesium sulfate. Removal of the solvent in vacuo and purification of the residue by flash chromatography on silica gel (hexane:ethyl acetate, 8:2) gave the title compound (2.99 g).

Step BB: 2-(methoxycarbonylmethyl)piperidine-1-carboxylic acid tert-butyl ester

To a solution of 2-(diazoacetyl)piperidine-1-carboxylic acid tert-butyl ester (5.90 g in 90 mL dry methanol) was added dropwise a solution of silver benzoate (265 mg in 3 mL triethylamine) and the mixture stirred at room temperature. After 2 hour, charcoal was added and the suspension filtered over diatomaceous earth. The mixture was concentrated in vacuo and the residue dissolved in ethyl acetate (400 mL), washed with water (2×100 mL) and brine (150 mL). The organic portion was dried over magnesium sulfate and the concentrate purified by flash chromatography on silica gel (hexane:ethyl acetate, 8:2) to give the title compound (5.47 g).

Step CC: 2-(2-hydroxyethyl)-piperidine-1-carboxylic acid tert-butyl ester

To a slurry of lithium aluminum hydride (580 mg in 65 mL dry diethyl ether) at 0° C. was added dropwise a solution of 2-(methoxycarbonylmethyl)piperidine-1-carboxylic acid tert-butyl ester (5.47 g in 40 mL dry diethyl ether) over a period of 30 minutes. The reaction was allowed to continue at 0° C. for an additional hour, at which time it was quenched by the careful addition of 0.58 mL water followed by 0.58 mL 2N sodium hydroxide and 1.8 mL water. The resulting suspension was stirred vigourously for 30 minutes then filtered through diatomaceous earth. The filtrate was concentrated in vacuo and the residue purified by flash chromatography on silica gel (hexane:ethyl acetate, 6:4) to give the title compound (4.61 g).

Thiophen-2-yl-acetyl chloride

To a solution of 2-thiophenyl acetic acid (150 mg in 2.5 mL dry methylene chloride) at 0° C. was added 0.004 mL N,N-dimethylformamide followed by the dropwise addition of 0.097 mL of oxalyl chloride. After 15 minutes the mixture was warmed to room temperature and stirred for an additional 2.5 hours. Removal of the solvents in vacuo provided the title compound which was used without purification.

Following a procedure similar to that described above, the following compounds were prepared:

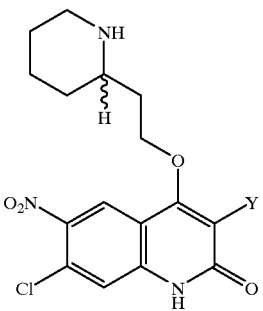

| Ex. # | Y | m/e |
|---|---|---|
| 1A | 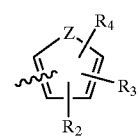 | |
| 1B | 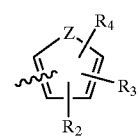 | 468 (M + H) |

What is claimed is:

1. A compound of the formula

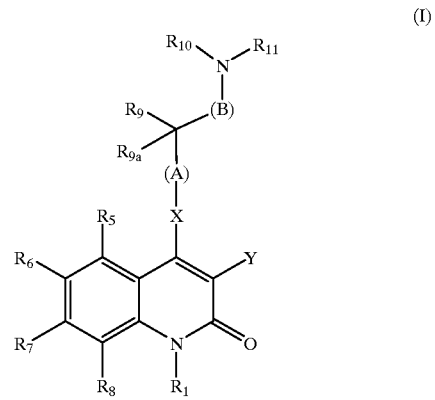

wherein:

A is a bond or $C_1$–$C_6$ alkyl;

B is a bond;

X is O;

Y is

Z is S;

$R_1$ is H or $C_1$–$C_6$ alkyl;

$R_2$, $R_3$ and $R_4$ are independently H, $C_1$–$C_6$ alkyl or halogen;

$R_5$, $R_6$, $R_7$ and $R_8$ are independently are H, halogen, $NO_2$ or $C_1$–$C_6$ alkyl;

$R_9$ and $R_{9a}$ are independently H or $C_1$–$C_6$ alkyl;

$R_{10}$ is H or $C_1$–$C_6$ alkyl;

$R_{11}$ is H or $C_1$–$C_6$ alkyl; or $R_9$ and $R_{10}$ can be taken together to form a six-membered ring with 5 carbons and 1 nitrogen atom;

or a pharmaceutically acceptable addition salt and/or hydrate thereof, or where applicable, a geometric or optical isomer or racemic mixture thereof.

2. The compound of claim 1 of the structural formula wherein Y is as indicated in the table below:

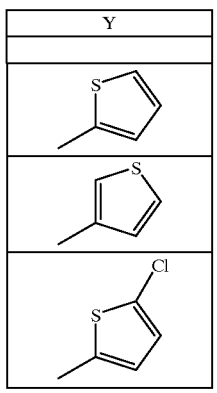

3. A pharmaceutical composition which comprises an effective amount of a compound as defined in claim 1 and a pharmaceutically acceptable carrier therefor.

4. A method for antagonizing gonadotropin-releasing hormone in a subject in need thereof which comprises administering to said subject an effective amount of a compound as defined in claim 1 to a subject suffering from a gonadotropin-releasing hormone derived disorder.

5. A method according to claim 4 wherein the gonadotropin-releasing hormone derived disorder is a sex-hormone related condition.

6. A method according to claim 4 wherein the gonadotropin-releasing hormone derived disorder is a sex hormone dependent cancer, benign prostatic hypertropy or myoma of the uterus.

7. A method according to claim 6 wherein the sex hormone dependent cancer is selected from the group consisting of prostatic cancer, uterine cancer, breast cancer and pituitary gonadotrophe adenomas.

8. A method according to claim 5 wherein the sex hormone related condition is selected from the group consisting of endometriosis, polycystic ovarian disease, uterine fibroids and precocious puberty.

9. A method for controlling pregnancy in a subject in need thereof which comprises administering an effective amount of a compound as defined in claim 1.

10. A method for treating lupus erythematosis in a subject in need thereof which comprises administering to said subject an effective amount of a compound as defined in claim 1.

11. A method for treating irritable bowel syndrome in a subject in need thereof which comprises administering to said subject an effective amount of a compound as defined in claim 1.

12. A method for treating premenstrual syndrome in a subject in need thereof which comprises administering to said subject an effective amount of a compound as defined in claim 1.

13. A method for treating hirsutism or polycycstic ovarian disease in a subject in need thereof which comprises administering to said subject an effective amount of a compound as defined in claim 1.

14. A method for treating short stature or a growth hormone deficiency in a subject in need thereof which comprises administering to said subject an effective amount of a compound which stimulates the endogenous production or release of growth hormone and an effective amount of a compound as defined in claim 1.

15. A method for treating sleep disorders in a subject in need thereof which comprises administering to said subject an effective amount of a compound as defined in claim 1.

16. A pharmaceutical composition which comprises an inert carrier and an effective amount of a compound which stimulates the endogenous production or release of growth hormone in combination with a compound as defined in claim 1.

17. A pharmaceutical composition made by combining the compound of claim 1 and a pharmaceutically acceptable carrier therefor.

18. A process for making a pharmaceutical composition comprising combining a compound of claim 1 and a pharmaceutically acceptable carrier.

19. The method of claim 15 wherein the sleep disorder is sleep apnea.

* * * * *